United States Patent

Haire et al.

[11] Patent Number: 5,871,692
[45] Date of Patent: Feb. 16, 1999

[54] METHOD AND APPARATUS FOR CLEANING, DECONTAMINATING, AND STERILIZING CATHETERS

[75] Inventors: Donna M. Haire, Garfield Heights; David F. Wolf-Bloom, Shaker Heights; Paul S. Malchesky, Painesville Twp., all of Ohio

[73] Assignees: Steris Corporation, Mentor; The Cleveland Clinic Foundation, Cleveland, both of Ohio

[21] Appl. No.: 782,647

[22] Filed: Jan. 14, 1997

[51] Int. Cl.$^6$ ........................................................ A61L 2/16
[52] U.S. Cl. .............................. 422/28; 422/34; 422/292; 422/300; 422/22; 604/266
[58] Field of Search .............................. 422/28, 292, 300, 422/34, 22; 604/266

[56] References Cited

U.S. PATENT DOCUMENTS

| | | | |
|---|---|---|---|
| D. 350,398 | 9/1994 | Campbell et al. | D24/217 |
| 3,893,843 | 7/1975 | Fry et al. | 134/10 |
| 4,713,402 | 12/1987 | Solomon | 523/112 |
| 4,721,123 | 1/1988 | Cosentino et al. | 134/57 R |
| 5,279,735 | 1/1994 | Cosentino et al. | 210/321.69 |
| 5,310,524 | 5/1994 | Campbell et al. | 422/33 |
| 5,425,815 | 6/1995 | Parker et al. | 134/26 |
| 5,476,454 | 12/1995 | Campbell | 604/283 |
| 5,508,046 | 4/1996 | Cosentino et al. | 424/616 |
| 5,580,530 | 12/1996 | Kawatsch et al. | 422/102 |
| 5,620,656 | 4/1997 | Wensky et al. | 422/28 |

FOREIGN PATENT DOCUMENTS

0592885 A2  4/1994  European Pat. Off. .

OTHER PUBLICATIONS

Cathetron Automated Catheter Reprocessing, Cathetron: The Only Catheter Reprocessing. No Date Available.

The Plain Dealer, "Hospitals Recycling Surgical Gear", Jan. 12, 1997.

*Primary Examiner*—Krisanne Thornton
*Assistant Examiner*—Fariborz Moazzam
*Attorney, Agent, or Firm*—Fay, Sharpe, Beall, Fagan, Minnich & McKee

[57] ABSTRACT

A method for cleaning, decontaminating, and sterilizing catheters (10) using a combination of liquid and gaseous/plasma sterilization techniques to ensure the complete and efficient sterilization of a catheter (10). Angiographic dye and saline are removed from the interior (36) of the balloon (14) and its lumen (16). The outer surfaces of the catheter (10) and a guide wire lumen (18) of the catheter (10) are cleaned, decontaminated, and sterilized (42) with a liquid sterilant. The liquid sterilant fills a balloon (14) and a balloon lumen (16) of the catheter (10). The liquid sterilant is retained in the balloon (14) and the lumen (16) for a select amount of time. Thereafter, the liquid sterilant is drained from the balloon (14) and the balloon lumen (16). The filling, retaining, and draining steps are repeated until an interior (36) of the balloon (14) and the balloon lumen (16) are sterilized. Residual liquid sterilant is rinsed from the interior (36) of the balloon (14) and the balloon lumen (16). The catheter (10) is dried and then a plasma or gaseous sterilant is used to sterilize at least the outer surfaces and the guide wire lumen (18) of the catheter (10).

15 Claims, 7 Drawing Sheets

METHOD AND APPARATUS FOR CLEANING, DECONTAMINATING, AND STERILIZING CATHETERS

BACKGROUND OF THE INVENTION

The present invention relates to the art of cleaning, decontaminating, and sterilizing medical instruments and devices. It finds particular application in conjunction with the cleaning, decontamination, and sterilization of previously used catheters, such as percutaneous transluminal coronary angioplasty catheters (PTCA catheters), for subsequent reuse and will be described with particular reference thereto.

As the costs associated with the delivery of effective healthcare continue to rise, there is a continuing effort on the part of doctors, healthcare facilities, and insurers to find ways of reducing these costs. The increasing popularity of single-use disposable medical devices has contributed to the increasing costs of surgery. The PTCA catheter is a widely used single-use disposable medical device used by surgeons to perform percutaneous transluminal angioplasty, a surgical procedure to clear blockages of plaque and the like from the arteries of a patient.

A percutaneous transluminal coronary angioplasty is carried out utilizing a PTCA catheter which typically takes the form of a balloon and a balloon lumen having a coaxial guide wire lumen passing therethrough. The proximal end of the PTCA catheter is bifurcated and includes a guide wire lumen port providing access to the guide wire lumen and a balloon lumen port providing access to the balloon lumen, and thus, the balloon. The distal end of the PTCA catheter includes the closed balloon which is sealed around the open end of the guide wire lumen, i.e., the guide wire lumen passes through the balloon and is open at its distal end. The surgeon uses a guide wire to guide the PTCA catheter into the vascular system of the patient to an area where a blockage exists. The catheter is often inserted into the femoral artery of the patient, and therefore, the catheter must be of a significant length (often 150 centimeters) to reach areas near the patient's heart.

After the catheter is in position, the surgeon inflates the balloon with a fluid, such as saline, by injecting the saline into the balloon lumen port of the catheter. Often, the saline includes a radiographic dye which enables the position and the inflated profile of the balloon to be monitored radiographically. The balloon expands radially and thus forces the arterial plaque radially outward into the wall of the artery. The surgeon then deflates the balloon, withdraws the catheter from the patient's vascular system, and disposes of the catheter.

Usually, more than one catheter is used on a particular patient, at a cost of several hundred dollars or more per catheter. Thus, a significant cost savings could be realized from the reuse of PTCA catheters. One difficulty associated with cleaning and sterilizing catheters such as PTCA catheters is attributable to a combination of the length of the catheter, the narrowness of the catheter and the guide wire and balloon lumens, and the closed balloon at the distal end of the catheter which does not allow liquid sterilant to be flushed through the balloon lumen and the balloon.

The cleaning of these devices by hand is time consuming and unreliable. Prior attempts to automate the process have resulted in unduly complex systems that have not been proven to be effective. Prior systems rely solely on liquid sterilization and are not compatible with gas sterilization techniques such as the use of ethylene oxide gas (EO) and these prior systems specifically teach away from the use of EO. Even with respect to the liquid sterilization utilized in the prior systems, the methods and apparatus disclosed do not control the "contact time" of the cleaning agent and the sterilant within the balloon and balloon lumen. They require the balloon to be pressurized with liquid sterilant and a cleaning agent an excessive number of times, reducing the remaining useful life of the balloon. Furthermore, merely filling the balloon lumen and balloon with a cleaning agent and sterilant and immediately flushing the same therefrom a selected amount of times, without further controls, has been found to be an ineffective cleaning and sterilization technique in certain circumstances.

One prior PTCA catheter sterilization method requires the liquid sterilized catheter to be rinsed of liquid sterilant immediately prior to use. This prior method requires a nurse or a surgical assistant to rinse the balloon and balloon lumen by injecting several syringes or more of sterile saline into the balloon. The saline that drains from the balloon and balloon lumen must be tested for the presence of sterilant using chemical test strips. The rinsing must be continued in this manner until the test strips indicate that the concentration of sterilant in the evacuated rinse fluid is below safe thresholds. It can be seen that the foregoing PTCA catheter sterilization method is time consuming and inconvenient. Also, the rinsing of the catheter just prior to its use results in a wet catheter being presented to the surgeon, which some surgeons may find objectionable.

Another disadvantage of known catheter sterilization systems is their requirement that a single catheter be processed or sterilized and stored in a specially designed cassette while awaiting use. These cassettes must be specially pressurized and capped in order for them to maintain the sterility of the catheter. Also, each cassette holds only one catheter, and thus, the efficiency of this prior system is necessarily limited.

The present invention provides a new and improved catheter cleaning, decontamination, and sterilization method and apparatus which overcomes the above-referenced problems and others.

SUMMARY OF THE INVENTION

In accordance with one aspect of the present invention, a method of cleaning, decontaminating, and sterilizing a catheter having a balloon and balloon lumen is described. Using a liquid decontaminant, at least the outer surfaces of the catheter are cleaned and decontaminated. The interior of the balloon and the balloon lumen are cleaned, decontaminated, and sterilized with a liquid sterilant or decontaminating agent. The catheter is dried and sterilized with a gaseous or plasma sterilant.

In accordance with another aspect of the present invention, a method of cleaning, decontaminating, and sterilizing a catheter having outer surfaces, a balloon, a balloon lumen, and a guide wire lumen, is provided. Using a liquid decontaminant, the outer surfaces of the catheter are cleaned and decontaminated and the guide wire lumen of the catheter is flushed. The balloon lumen and the interior of the balloon are cleaned, decontaminated, and sterilized with a liquid sterilant. The catheter is dried and thereafter, at least the outer surfaces and the guide wire lumen of the catheter are sterilized with a gaseous or plasma sterilant.

In accordance with a more limited aspect of the present invention, the step of sterilizing the balloon lumen and the interior of the balloon of the catheter includes rinsing the dye and saline from within the balloon and the balloon lumen. Liquid sterilant is communicated into the interior of the balloon and into the balloon lumen and retained in the balloon and balloon lumen for a selected amount of time. The liquid sterilant is then drained from the balloon and balloon lumen of the catheter. The filling, retention, and draining steps are repeated until the interior of the balloon and the balloon lumen are sterilized.

In accordance with another aspect of the present invention, a method of washing a catheter having outer surfaces, a balloon, a balloon lumen, and a guide wire lumen is provided. The outer surfaces and the guide wire lumen of the catheter are cleaned and decontaminated. The interior of the balloon and the balloon lumen are cleaned, decontaminated, and sterilized with a liquid sterilant and the catheter is dried. Finally, the catheter is packaged and then exposed to a gaseous or plasma sterilant.

In accordance with yet another aspect of the present invention, an apparatus for cleaning, decontaminating, and sterilizing at least the balloon lumen and the interior of the balloon of a plurality of catheters is provided. The apparatus includes a supply of liquid sterilant and a liquid bath for receiving a plurality of catheters therein to maintain the catheters at a selected temperature. A manifold is in selective fluid communication with the liquid sterilant supply and includes a plurality of catheter connection fittings for connecting the balloon lumen of each of the plurality of catheters in fluid communication with the manifold. A pump pumps liquid sterilant under pressure from the supply of liquid sterilant into the balloon lumen and balloon of each of the plurality of catheters connected to the manifold and also evacuates the liquid sterilant from the balloon and the balloon lumen of each of the plurality of catheters. At least one valve selectively blocks the flow of liquid sterilant to and from the manifold. An electronic controller is connected to the pump and the at least one valve for controlling the operation of the pump and the at least one valve.

One advantage of the present invention is the more effective cleaning and sterilization of catheters.

Another advantage of the present invention is the efficiency and ease with which catheters are sterilized.

Another advantage of the present invention is the combination of liquid and gas or plasma sterilization techniques to effectively sterilize catheters.

Another advantage of the present invention is the elimination of the need to sterilize and store the catheters in special pressurized containers.

Another advantage of the present invention is that the sterilized catheters are rinsed, dried, and ready for immediate use without further rinsing or preparation.

Another advantage of the present invention is the ability to simultaneously sterilize the interior of the balloon and the balloon lumen of each of a plurality of catheters.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1A:
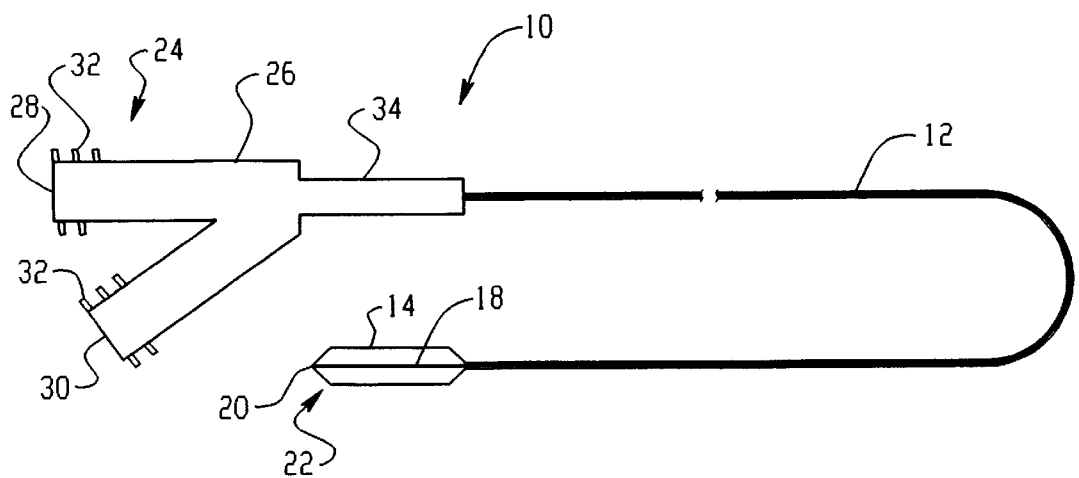
FIG. 1A shows a PTCA catheter suitable for being sterilized in accordance with the method and apparatus of the present invention.
Figure 1B:
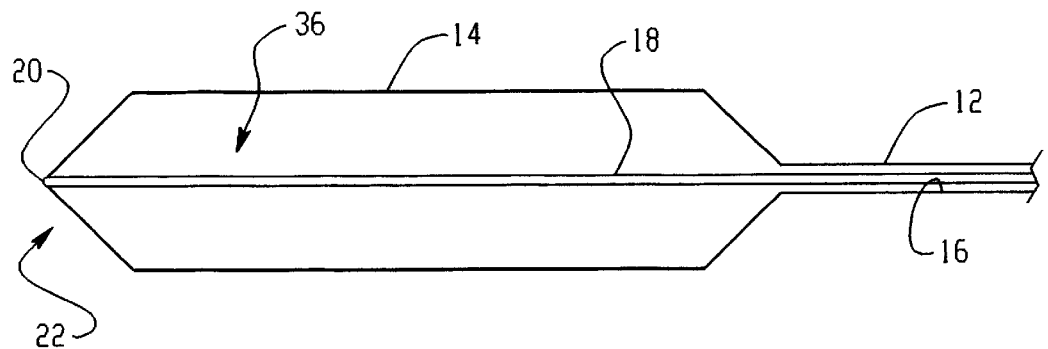
FIG. 1B is a partial enlarged diagrammatic illustration of distal portion of the PTCA catheter of FIG. 1, including the balloon, balloon lumen, and guide wire lumen thereof.

With reference to FIGS. 1A and 1B, a percutaneous transluminal coronary angioplasty (PTCA) catheter 10 includes an elongated and flexible tubular member 12 with a balloon 14 located at the distal end. As is seen most clearly in FIG. 1A, the tubular member 12 provides a channel or lumen 16 to the balloon 14. A through-lumen, referred to as a guide wire lumen 18, is coaxially positioned within balloon lumen 16 and extends through balloon 14 to an open distal end 20. The balloon 14 is closed at its distal end 22 around the guide wire lumen 18.

The tubular member 12 of the catheter 10 has a proximal end 24 including a bifurcated hub 26. The bifurcated hub 26 includes a guide wire lumen access port 28 providing access to the guide wire lumen 18 and a balloon lumen access port 30 providing access to the balloon lumen 16, and thus to the balloon 14. Each port 28, 30 typically includes commonly known luer lock connectors 32 or the equivalent. As shown herein, the bifurcated hub 26 is connected to the tubular member 12 through a strain relief sheath 34 for a more durable interconnection. The illustrated PTCA catheter 10 is an example of a catheter that can be cleaned, decontaminated, and sterilized utilizing a method and apparatus in accordance with the present invention. Those skilled in the art will recognize that the PTCA catheter 10 may be modified but will remain suitable for sterilization in accordance with the present invention, and that a sterilization method and apparatus in accordance with the present invention may be utilized to clean and sterilize other catheters having a balloon and balloon lumen as described above.

During angioplasty procedures, the tubular member 12 of the catheter 10 is inserted into the vascular system of the patient, and thus, the outer surfaces of the catheter 10, including the outer surfaces of the hub 26, the strain relief sheath 34, the tubular member 12, and the balloon 14 become contaminated with the blood and other bodily fluids of the angioplasty patient. Furthermore, the guide wire lumen 18, which is open at the distal end 20, also becomes contaminated with the patient's blood. In most angioplasty procedures, the balloon lumen 16 and the interior 36 of the balloon 14 will not become contaminated with the patient's bodily fluids. In subsequent angioplasty procedures, any contamination within the balloon 14 would not be readily transmissible into the blood of the later patient in light of the closed nature of the balloon. However, the balloon 14 may burst upon inflation in a later procedure, and for this and other reasons, the safe sterilization of PTCA catheters 10 includes a complete sterilization of the balloon lumen 16 and the interior 36 of the balloon 14.

Furthermore, during angioplasty procedures, an angiographic dye and saline mixture is communicated into the interior 36 of the balloon 14. This dye and saline mixture are removed from the interior 36 of the balloon 14 within a relatively short time (less than 24 hours) lest it crystallizes, adversely affecting the utility of the catheter 10 for subsequent angioplasty procedures. The method and apparatus of the present invention result in the sterilization of an entire PTCA catheter 10, including all of the outer surfaces, as well as the guide wire lumen 18, the balloon lumen 16, and the interior 36 of the balloon 14.

Figure 2:
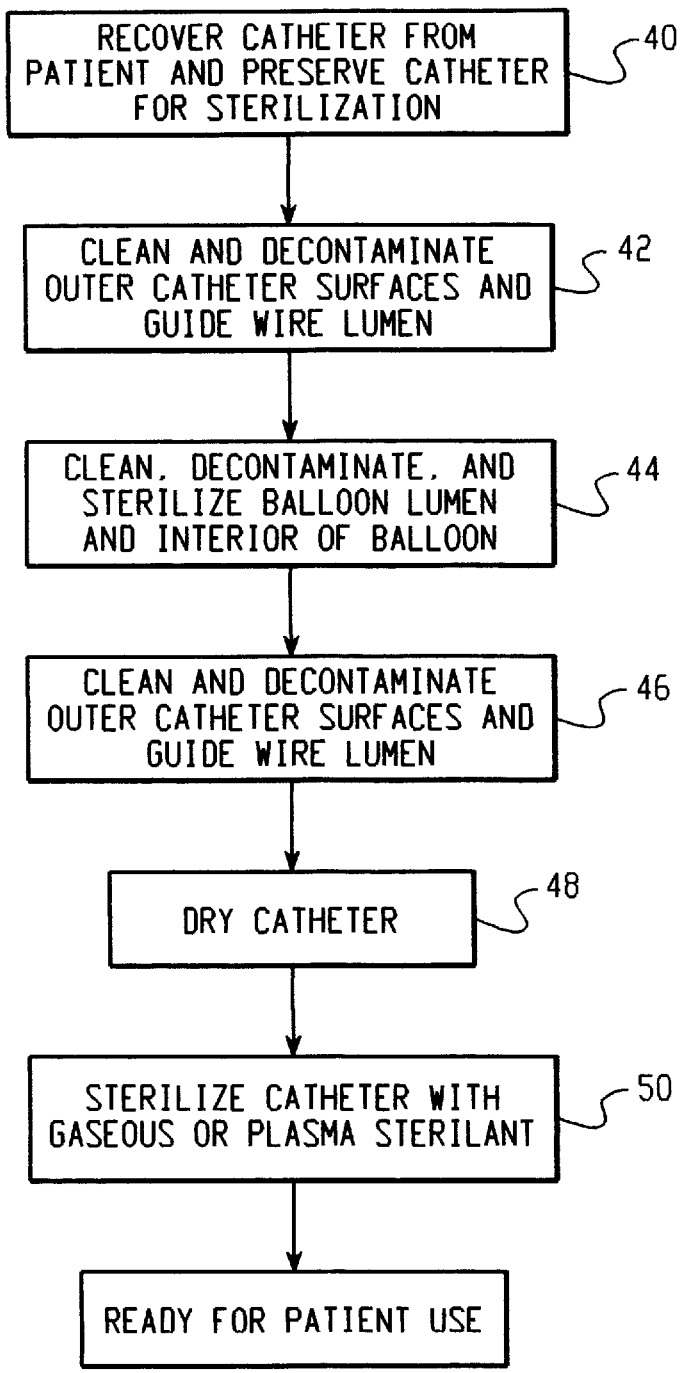
FIG. 2 is a flow chart illustrating catheter cleaning and sterilization in accordance with the present invention.

With reference to FIG. 2, the preferred overall method of sterilizing a PTCA catheter 10 is shown. Each step or means shown in FIG. 2 is described in further detail with reference to FIGS. 3–6. In a step 40 the catheter 10 is recovered from the patient and preserved for sterilization. Once the catheter 10 has been recovered and preserved for later sterilization, a step or means 42 cleans and decontaminates the outer surfaces and the guide wire lumen 18 of the catheter 10. Following the cleaning and decontamination of the outer surfaces and the guide wire lumen 18 of the catheter 10, a step or means 44 cleans, decontaminates, and sterilizes the balloon lumen 16 and the interior 36 of the balloon 14 of the catheter 10. Preferably, a step or means 46 provides a second cleaning and decontamination of the outer surfaces and the guide wire lumen 18 of the catheter 10. A step or means 48 dries the catheter 10, and a step or means 50 sterilizes the catheter with a gaseous sterilant, resulting in a completely sterilized catheter that is free of harmful amounts of residual sterilant, dry, and ready for reuse.

Figure 3:
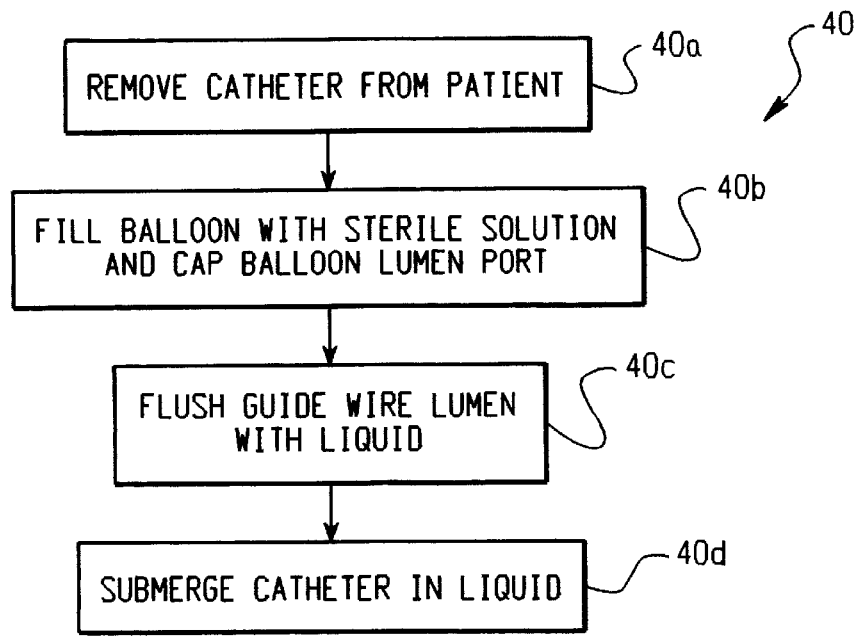
FIG. 3 is a flow chart illustrating removing the catheter from the patient and preserving the catheter for sterilization in accordance with the present invention.

With reference to FIG. 3, the step 40 of recovering the catheter 10 from the patient is shown in greater detail and includes steps or means 40a–40d. In a step 40a, the catheter 10 is removed from the patient. This step is generally performed manually. Immediately following the removal of the catheter 10 from the patient, a step or means 40b fills the balloon 14 of the catheter 10 with a sterile liquid, such as sterile saline, sterile water, or the like, and caps the balloon lumen port 30 of the catheter 10 to retain the sterile liquid in the balloon 14 and balloon lumen 16. The sterile liquid in the balloon 14 and balloon lumen 16 and the capping of the lumen port 30 prevents the angiographic dye and saline within the balloon 14 from crystallizing. Furthermore, capping the balloon lumen port 30 not only prevents the escape of the sterile fluid from the balloon 14, but also prevents the contamination of the interior 36 of the balloon 14 with blood and other contaminates that are in the guide wire lumen 18 and on the outer surfaces of the catheter 10.

A step or means 40c flushes the guide wire lumen 18 with a liquid and a step or means 40d submerges or otherwise surrounds the catheter 10 with a liquid. Although ordinary saline or the like may be utilized as the liquid in the step or means 40c and the step or means 40d, the liquid utilized is preferably an anticoagulant liquid solution. One suitable solution used in the steps or means 40c and 40d is a solution of 10,000 units of Heparin per 1000 milliliters (ml.) of saline. With such a solution, the guide wire lumen 18 of the catheter 10 is flushed with approximately 10 ml. of the solution and the catheter is then submerged in the solution for approximately 15 minutes. The anticoagulant solution rinses blood and the like from the outer surfaces of the catheter 10 and from within the guide wire lumen 18. It also prevents the clotting and hardening of the blood on the catheter 10 and in the guide wire lumen 18. Those skilled in the art will recognize that the capped balloon lumen port 30 prevents the contamination of the interior 36 of the balloon 14 with blood when the catheter 10 is treated with the anticoagulant solution. Once the catheter 10 has been recovered from the patient and treated as described, an indefinite amount of time may pass. The catheter 10 can remain submerged in a bath of liquid as described. In practice, the catheter sterilization process continues relatively quickly following the recovery of the catheter 10 from the patient.

Figure 4:
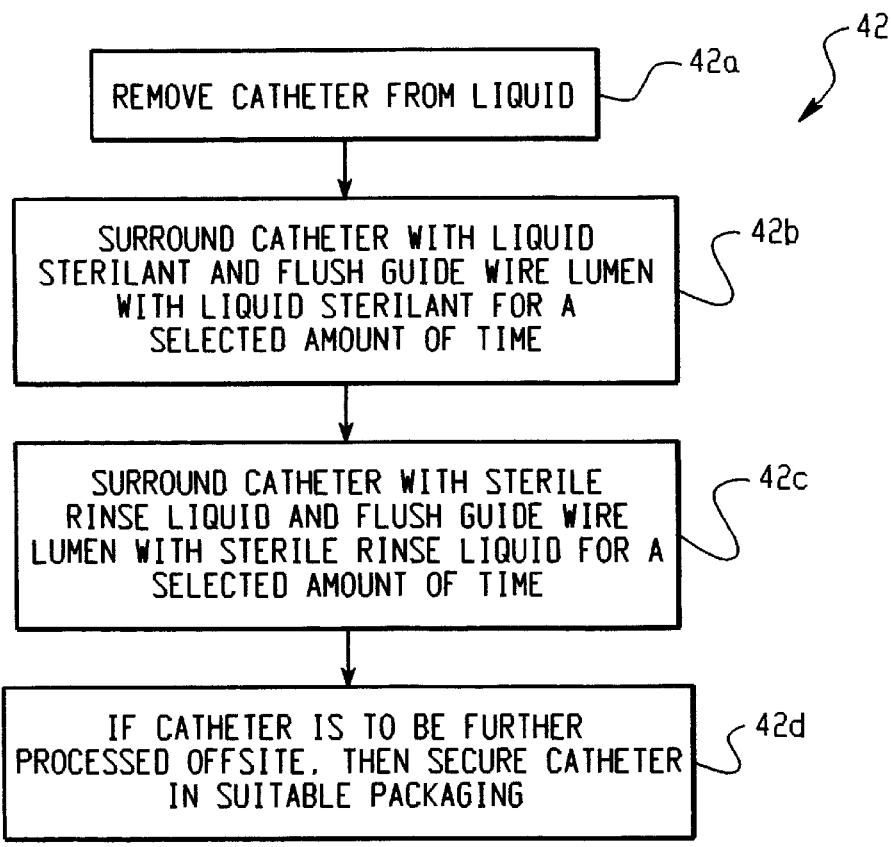
FIG. 4 is a flow chart illustrating performing the first cleaning and decontamination of the catheter.

With reference to FIG. 4, the sterilization process continues with the step or means 42 cleaning and decontaminating the outer surfaces and the guide wire lumen 18 of the catheter 10. The balloon lumen port 30 remains capped at this point in the sterilization process. A step or means 42a removes the catheter 10 from the anticoagulant liquid and a step or means 42b surrounds the catheter 10 with liquid sterilant, decontaminant, or disinfectant and flushes the guide wire lumen 18 with liquid sterilant, decontaminant, or disinfectant for a selected amount of time.

Thereafter, a step or means 42c rinses the outer surfaces and the guide wire lumen 18 of the catheter 10 with a sterile rinse liquid such as sterile water. While the step or means 42 decontaminates the outer surfaces of catheter 10 and also facilitates the decontamination of the guide wire lumen 18, additional steps are provided as described below to ensure the decontamination of these areas of catheter 10. A preferred apparatus for rinsing and decontaminating the interior surfaces of the catheter 10 is illustrated in U.S. Pat. Nos. 4,731,222, 4,892,706, 5,116,575, and 5,217,698 of an assignee herein.

The process either continues immediately with the step or means 44 to sterilize the balloon lumen 16 and the interior 36 of the balloon 14 or a step or means 42d places the catheter 10 in a suitable temporary storage container, such as a sealable biohazard bag, for later processing. The step or means 42d is utilized when further processing is conducted at a different site. Also, a hospital may wish to accumulate a large number of catheters for subsequent processing in a batch as is described below.

Figure 5:
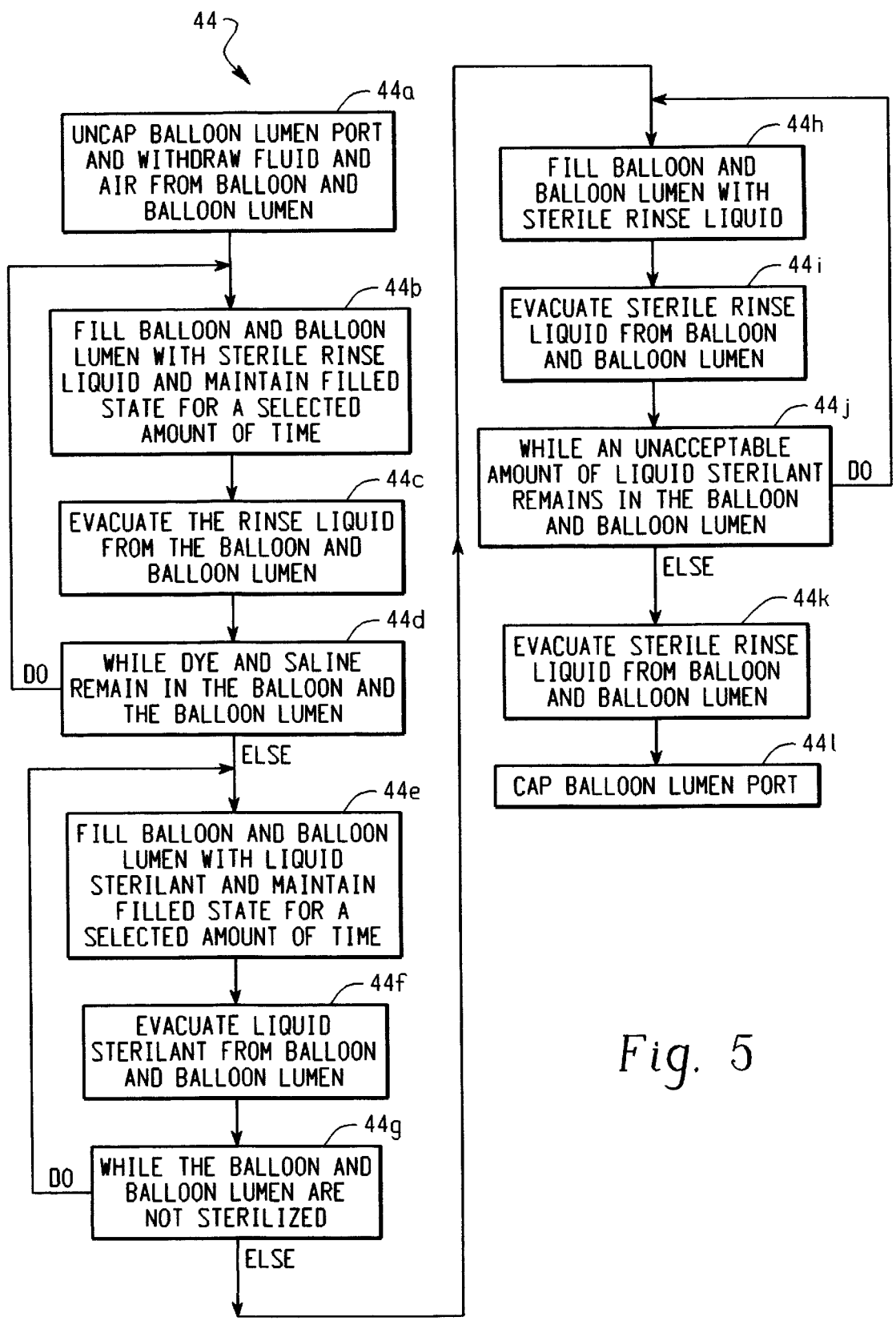
FIG. 5 is a flow chart illustrating cleaning, decontaminating, and sterilizing the balloon lumen and interior of the balloon.

As is shown in detail in FIG. 5, the reprocessing continues with the step or means 44 to clean, decontaminate, and sterilize the balloon lumen 16 and the interior 36 of the balloon 14. A step or means 44a uncaps the balloon lumen port 30 and withdraws the sterile fluid and any air from the balloon 14 and balloon lumen 16. Because the angiographic dye and saline communicated into the interior 36 of the balloon 14 and the balloon lumen 16 during the angioplasty procedure can interfere with the biocidal action of the liquid sterilant and the further use of the catheter 10, the sterilization of the balloon 14 and the balloon lumen 16 involves the removal of the dye and saline. A step or means 44b fills the balloon 14 and the balloon lumen 16 with a sterile rinse liquid, such as sterile water. The sterile water may optionally be retained within the balloon 14 and the lumen 16 for a selected "contact time" to facilitate the rinsing process. A step or means 44c evacuates the sterile rinse fluid from the balloon 14 and the balloon lumen 16 and a step or means 44d repeats the filling and evacuating steps 44b, 44c until the dye and saline are removed from the balloon 14 and the balloon lumen 16. It has been found that repeating the steps 44b, 44c at least fifteen and preferably twenty times, with an optional contact time of approximately fifteen—thirty seconds is effective for removing the dye and saline from the interior 36 of the balloon 14 and from the balloon lumen 16.

In order to sterilize the interior 36 of the balloon 14 and the balloon lumen 16, a liquid sterilant is fed into the balloon 14 and the balloon lumen 16. While simply repeatedly filling the balloon 14 and the lumen 16 with liquid sterilant and immediately evacuating the same may sterilize the interior 36 of the balloon 14 and the lumen 16, it has been found that such a method does not sterilize the interior 36 of the balloon 14 and the balloon lumen 16 as effectively as repeatedly filling the balloon 14 and balloon lumen 16 with the liquid sterilant, retaining the liquid sterilant in the balloon 14 and balloon lumen 16 for a selected amount of time, and thereafter evacuating the liquid sterilant from the balloon 14 and the balloon lumen 16. This increase in "contact time" or the amount of time that the liquid sterilant is in contact with the interior 36 of the balloon 14 and the balloon lumen 16 results in more effective sterilization. It has also been found that filling the balloon 14 once with liquid sterilant and holding it filled for a selected duration is less effective than filling and emptying the balloon several times over the same selected duration.

Therefore, a step or means 44e fills the balloon 14 and the balloon lumen 16 with a liquid sterilant and maintains the filled state of the balloon 14 for a selected amount of time. A step or means 44f evacuates the liquid sterilant from the balloon 14 and lumen 16 and a step or means 44g repeats the step 44e and the step 44f until the interior 36 of the balloon 14 and the balloon lumen 16 are sterilized. For example, it has been found that $10^6$ colony forming units of spores are killed or removed from the interior 36 of the balloon 14 and the balloon lumen 16 by repeating the steps 44e and 44f at least eight times with a contact time of at least approximately two minutes. It is preferable to repeat the steps 44e and 44f at least ten times using a contact time of at least approximately one and one half minutes using a 0.2% peracetic acid sterilant. By way of example, the interior 36 of a balloon 14 and a balloon lumen 16 of a catheter 10 were inoculated with $10^6$–$10^7$/0.5 ml. *B. subtilis* spores using different carrier solutions of water, saline, and 10% serum/ 90% saline. A 0.2% peracetic acid sterilant was utilized. Sterilization was not achieved, with the water carrier, when steps 44e and 44f were repeated as follows: one time with a contact time of five minutes; two times with a contact time of seven minutes; three times with a contact time of one minute; five times with a contact time of one minute; and, ten times with a contact time of 1 minute (3 out of four trials not sterile). Sterilization was achieved, with the water carrier, when steps 44e and 44f were repeated as follows: four times with a contact time of two minutes; twenty-two times with a contact time of 0.25 minutes; and, twenty-four times with a contact time of 0.25 minutes. Using the serum and saline carrier solution which presents the most difficult sterilization situation, when steps 44e and 44f were repeated ten times with a contact time of at least 1.5–2 minutes, sterilization resulted for seven of the nine trials. With the saline carrier, six trials were conducted and steps 44e and 44f were repeated ten times with a contact time of two minutes. All six trials resulted in sterilization.

Following the sterilization of the interior 36 of the balloon 14 and the balloon lumen 16 using the liquid sterilant as described, the liquid sterilant is rinsed from the interior 36 of the balloon 14 and from the balloon lumen 16. Rinsing the interior 36 of the balloon 14 and the balloon lumen 16 is preferably accomplished by repeatedly filling the balloon 14 and the balloon lumen 16 with a sterile rinse liquid, such as sterile water, and thereafter immediately evacuating the rinse liquid from the balloon 14 and the balloon lumen 16. A step or means 44h fills the balloon 14 and the balloon lumen 16 with a sterile rinse liquid. A step or means 44i evacuates the sterile rinse liquid from the balloon 14 and lumen 16 after the selected amount of time has passed. A step or means 44j causes the means 44h and 44i to repeat the filling and evacuating steps until the amount of residual sterilant in the interior 36 of the balloon 14 and in the balloon lumen 16 is below the selected threshold.

For example, using a peracetic acid sterilant and a sterile rinse liquid of sterile deionized/filtered water, it has been found that repeating steps 44h and 44i at least fifteen times, and preferably twenty times, results in the interior 36 of the balloon 14 and the lumen 16 being essentially free of residual sterilant. Once the rinsing process is complete, a step or means 44k evacuates the sterile rinse liquid from the balloon 14 and its lumen 16 and a step or means 44l caps the balloon lumen port 30 to prevent recontamination.

Figure 6:
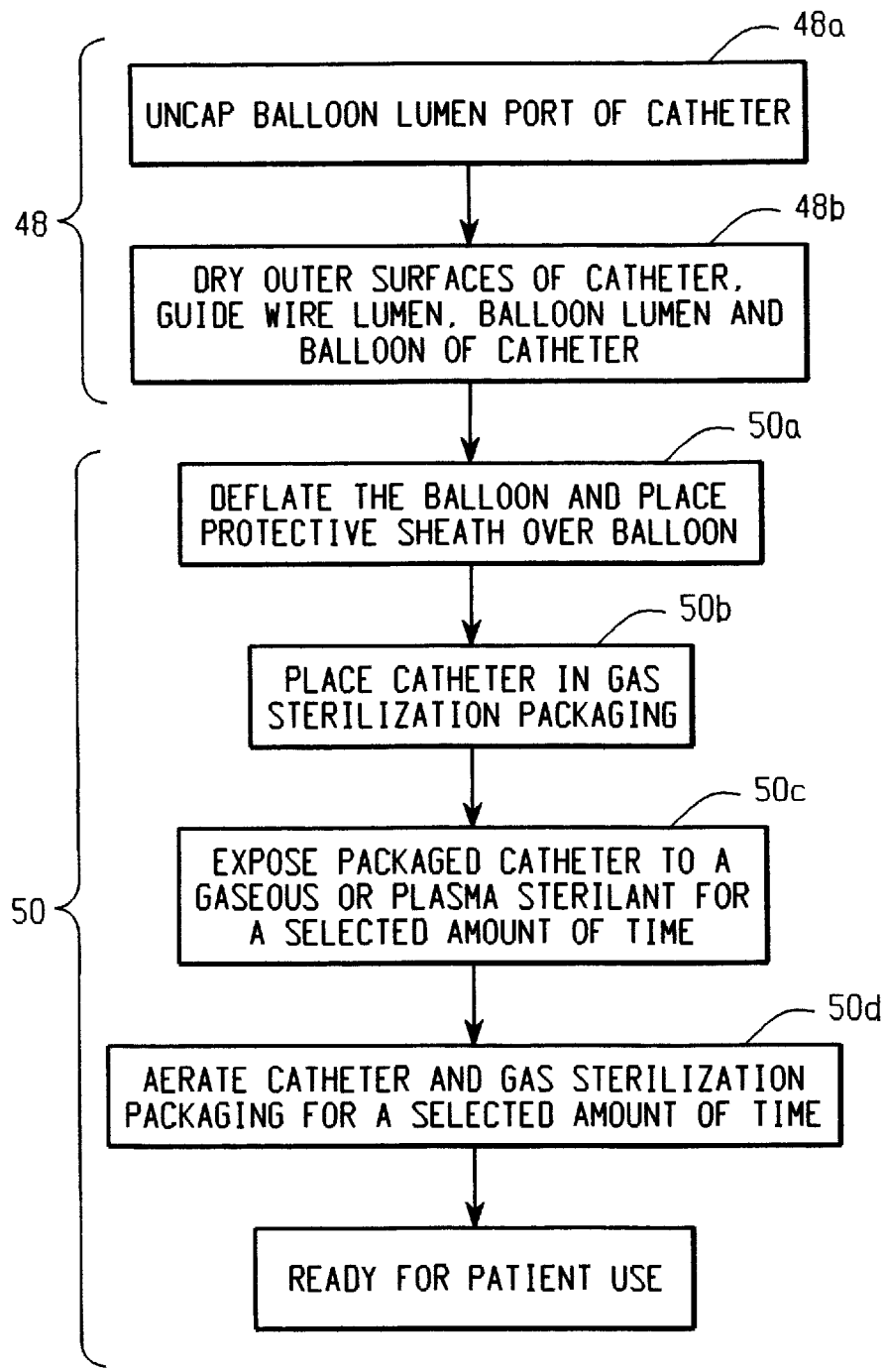
FIG. 6 is a flow chart illustrating the gaseous or plasma sterilization of the catheter.

In case of any contamination of the catheter 10 during transport or handling with respect to the above procedures, it is preferable to provide an optional step or means 46 for a second cleaning and decontamination of the outer surfaces and the guide wire lumen 18 of the catheter 10. The step or means 46 performs substantially the same operations as the step or means 42 as described above in detail with reference to FIG. 4. The step or means 46 ensures that the outer surfaces of the catheter 10 are decontaminated and facilitates the sterilization of the guide wire lumen 18. Following the second cleaning and decontamination of the outer surfaces and the guide wire lumen 18 of the catheter 10 with a liquid sterilant, the catheter 10 is completely dried by a step or means 48 in preparation for a step or means 50 to gas sterilize the catheter 10. As is shown in FIG. 6, a step or means 48a uncaps the balloon lumen port 30 of the catheter 10. A step or means 48b dries the outer surfaces, the guide wire lumen 18, the balloon lumen 16, and the interior 36 of the balloon 14. The step or means 48b is preferably carried out in a sterile vacuum oven system with −25 to −30 inches of mercury (Hg) at a temperature of 30 degrees C to 40 degrees C for 1.5 hours. Alternatively, the oven can be a non-sterile vacuum oven system.

With continuing reference to FIG. 6, once the catheter 10 is dry, the step or means 50 gas sterilizes the catheter 10, and in particular the outer surfaces and the guide wire lumen 18 thereof, preferably using a gaseous or plasma sterilant such as ethylene oxide (EO) gas, vapor phase hydrogen peroxide, or the like. A step or means 50a deflates the balloon 14 and places a protective sheath over the balloon 14. A step or means 50b places the catheter in gas sterilization packaging, such as a standard EO sterilization bag. A step or means 50c exposes the packaged catheter 10 to a plasma or gaseous sterilant such as EO for a selected amount of time. For example, the step or means 50c exposes the catheter 10 to 100% EO for approximately 4 to 5 hours at 90 degrees F. A 4.75 hour EO exposure time has been found to be effective. Following the exposure of the catheter 10 to EO, a step or means 50d aerates the catheter 10 and the packaging to disperse residual gaseous sterilant. It has been found effective for the step or means 50d to aerate the catheter 10 and the gas sterilization packaging for 12 hours at approximately 90 degrees F. The catheter 10 can then be safely reused for another angioplasty procedure with a different patient.

Figure 7:
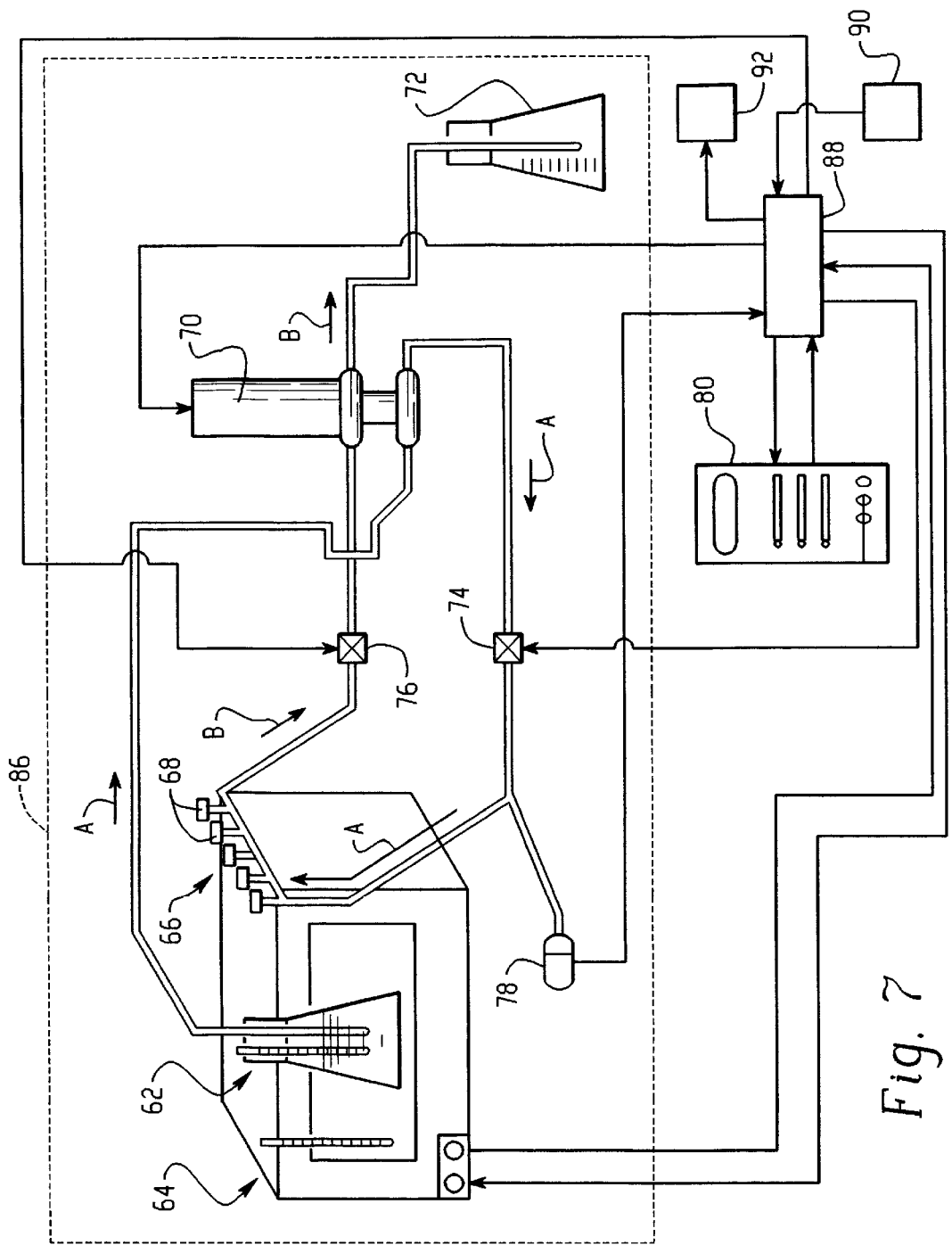
FIG. 7 is a schematic view of a balloon and balloon lumen pump system as it is configured for liquid sterilization of the balloon and balloon lumen.

With reference to FIG. 7, a supply of liquid sterilant 62 is heated in a water bath 64. The heated water bath 64 also receives a plurality of the catheters 10 during the sterilization process. The liquid sterilant, such as the 0.2% peracetic acid, is utilized at a temperature of 40–60 degrees C, preferably 50–56 degrees C. The heated water bath 64 heats the supply of liquid sterilant 62 and the catheters 10 placed in the bath 64 to the optimum operative temperature of the selected sterilant. A manifold 66 includes a plurality of catheter connection fittings 68 for fluidically connecting the balloon lumen port 30 of each of the plurality of catheters 10 to the manifold 66.

The manifold 66 is in fluid communication with the supply of liquid sterilant 62 through a pump 70 and is also in fluid communication with a liquid sterilant disposal reservoir 72 through the pump 70. The liquid sterilant is pumped by the pump 70 from the supply 62 into the manifold 66 as indicated by the arrows A and is pumped from the manifold 66 to the disposal reservoir 72 as indicated by the arrows B. An inlet valve 74 and an outlet valve 76 selectively block the flow of fluid to and from manifold 66. A pressure transducer 78 monitors the pressure of the fluid in the manifold 66. A display 80 displays process parameters and information regarding the balloon and balloon lumen sterilization process to the operator of the apparatus. The parameters preferably include the date, the time, the sterilant and water bath temperatures, the number of balloon inflation cycles, the duration of each balloon inflation cycle, and the like. Also, the apparatus is preferably enclosed within a fume hood or another suitable enclosure 86 to minimize the escape of sterilant vapors into the atmosphere, and to minimize environmental contamination of the water bath 64, the supply of sterilant 62, and the supply of sterile rinse fluid 82 (FIG. 8).

Figure 8:
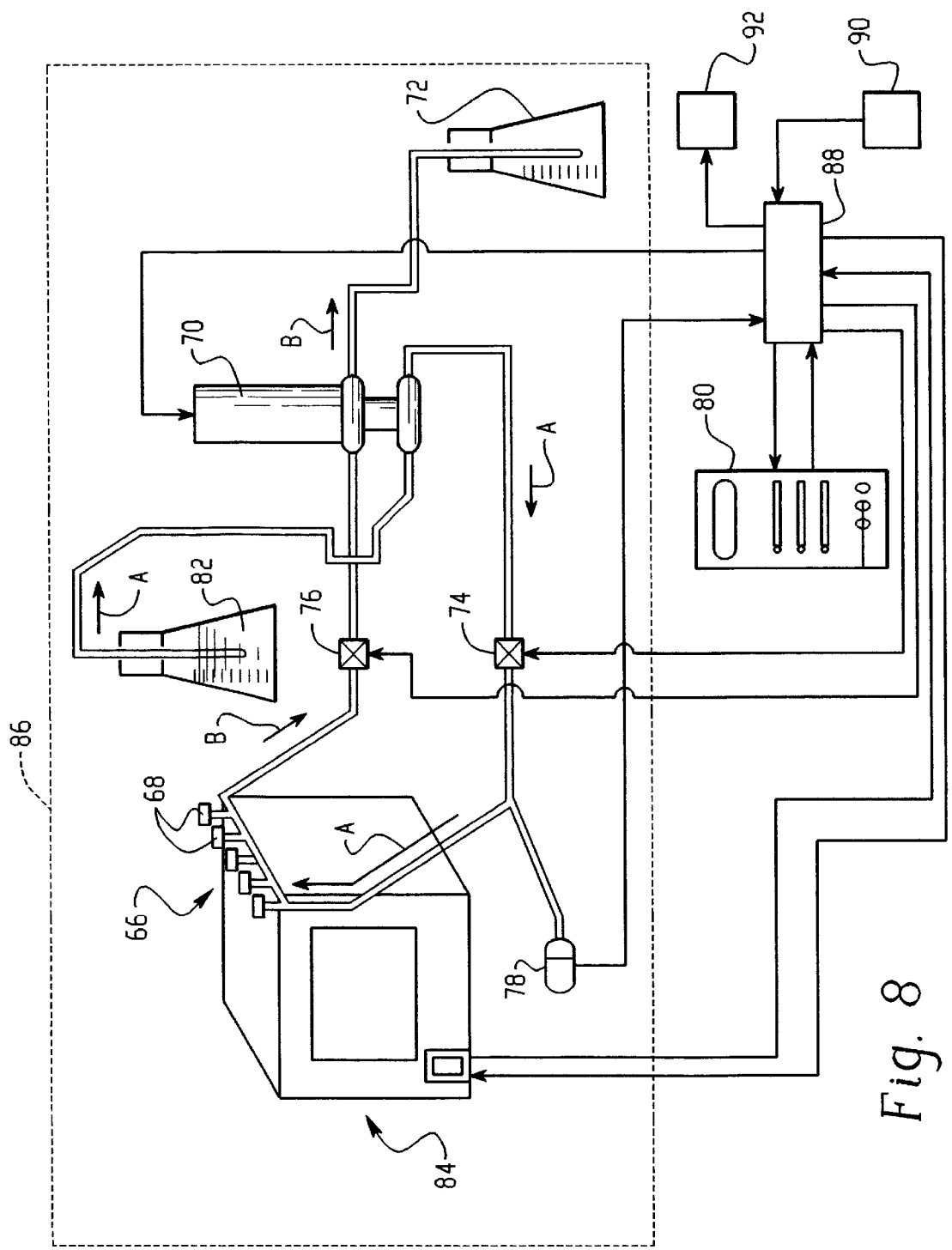
FIG. 8 is a schematic view of a balloon and balloon lumen pump system as it is configured for rinsing the balloon and balloon lumen.

FIG. 8 schematically shows a reconfiguration of the apparatus of FIG. 7 during the rinsing steps 44b–44d and 44h–44j in which the angiographic dye and saline mixture, and the liquid sterilant, are respectively rinsed from the interior 36 of the balloons 14 and the balloon lumens 16 of each catheter 10 connected to the fittings 68 of manifold 66. A supply of sterile rinse liquid 82 is in fluid communication with the manifold 66 through the pump 70 and the manifold 66 is also in fluid communication with the disposal reservoir 72. The sterile rinse liquid is pumped from supply 82 to manifold 66 through conduits as shown by the arrows A, and the sterile rinse liquid is pumped from the manifold 66 to the disposal reservoir 72 through conduits as indicated by the arrows B. For rinsing operations, each catheter 10 connected to the manifold 66 is preferably submerged in an ultrasonic water bath 84.

The water baths 64,84, the pump 70, the valves 74,76, the pressure transducer 78, and the visual display 80 are all electrically connected to an electronic controller 88 that controls the operation of each of the noted components. The electronic controller 88 controls the application of heat and ultrasonic waves to the baths 64,84. The electronic controller 88 also selectively operates the pump 70 as required to pump sterilant and sterile rinse liquid, and monitors the fluid pressure in the manifold 66 through electrical signals received from the transducer 78. The controller 88 selectively opens and closes the valves 74,76 to selectively block the flow of liquid sterilant and rinse liquid to and from the manifold 66 and the disposal reservoir 72, and displays process parameters and information to an operator on the display 80. An input system 90 is connected to the electronic controller 88 for operator input of data and for operator control. A printer 92 prints out the date and time, the operator, and cycle information to provide written documentation for each catheter 10. The cycle information includes such information as the number of balloon inflations with the liquid sterilant, the duration of sterilant contact, the number of rinse cycles, and the like.

The electronic controller 88 is programmed to operate the apparatus in accordance with the step 44 as described above with reference to FIGS. 2 and 5. Through the operation of the pump 70 and the valves 74,76, the electronic controller 88 controls the flow of liquid sterilant and rinse liquid into and out of the balloon 14 and balloon lumen 16 of each catheter 10 connected to the manifold 66 and controls the contact time of the liquid sterilant and the rinse liquid within the balloon 14 and balloon lumen 16.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of cleaning, microbially decontaminating, and sterilizing an elongated catheter having an elongated balloon lumen open at a first end and closed by a balloon at a second end, said method comprising:
    (a) cleaning and microbially decontaminating at least the outer surfaces of the catheter with a liquid;
    (b) rinsing the interior of the balloon and the balloon lumen with a sterile rinse liquid to rinse any dye and saline from the balloon and the balloon lumen;
    (c) communicating liquid sterilant into the interior of the balloon and into the balloon lumen;
    (d) retaining the liquid sterilant in the balloon and balloon lumen for at least one minute;
    (e) draining the liquid sterilant from the balloon and the balloon lumen,
    (f) repeating steps (c)–(e) a plurality of times until the interior of the balloon and the balloon lumen are sterilized;
    (g) drying the catheter in the presence of heat and a vacuum;
    (h) placing the dry catheter in gas permeable sterilization packaging and sterilizing the thus packaged catheter with gaseous ethylene oxide for at least approximately four hours; and,
    (i) storing the sterile and dry catheter in the packaging for subsequent direct use.

2. The method as set forth in claim 1 wherein step (f) includes repeating steps (c)–(e) at least eight times and wherein step (d) includes retaining the liquid sterilant in the balloon and in the balloon lumen for at least two minutes.

3. The method as set forth in claim 1 wherein the cleaning and decontaminating step (a) includes:
    blocking the balloon lumen to prevent the entrance of the liquid decontaminant into the balloon lumen and the interior of the balloon;
    heating a bath of the liquid decontaminant to a temperature of greater than 40 decrees c;
    immersing the catheter in the heated bath of liquid decontaminant for a selected amount of time; and,
    flushing the liquid decontaminant through the guide wire lumen of the catheter for a selected amount of time.

4. The method as set forth in claim 3 further including repeating the cleaning and decontaminating step (a) following the step (f).

5. A method of cleaning microbially decontaminating, and sterilizing a catheter having outer surfaces, a balloon, a dead-end balloon lumen, and a guide wire lumen, said method comprising:
    (a) injecting a sterile fluid into the balloon and balloon lumen of the catheter to prevent crystallization of radiographic dye in the balloon and balloon lumen;

(b) blocking the balloon lumen of the catheter to prevent the sterile fluid from escaping the balloon and balloon lumen;

(c) wetting the outer surfaces and the guide wire lumen of the catheter with liquid anticoagulant solution to rinse blood from and prevent clotting of blood on the outer catheter surfaces and in the guide wire lumen;

(d) cleaning and decontaminating the outer surfaces of the catheter and flushing the guide wire lumen of the catheter with a liquid microbial decontaminant;

(e) rinsing the interior of the balloon and the balloon lumen with a sterile rinse liquid to rinse any dye and saline from the balloon and the balloon lumen;

(f) communicating liquid sterilant into the interior of the balloon and into the balloon lumen;

(g) retaining the liquid sterilant in the balloon and balloon lumen for a selected amount of time;

(h) draining the liquid sterilant from the balloon and the balloon lumen;

(i) repeating steps (f)–(h) a plurality of times until the interior of the balloon and the balloon lumen are sterilized;

(j) drying the catheter; and, (k) sterilizing at least the outer surfaces and the guide wire lumen of the dry catheter with a gaseous or plasma sterilant.

6. The method as set forth in claim 5 further comprising, before the drying step:

(i-1) rinsing the balloon and balloon lumen with a sterile rinse liquid after sterilizing the balloon lumen and the interior of the balloon until the concentration of sterilant in the balloon and balloon lumen is below a predetermined threshold.

7. The method as set forth in claim 6 wherein said rinsing step (i-1) includes:

(i-1a) communicating a sterile rinse liquid into the interior of the balloon and into the balloon lumen;

(i-1b) retaining the sterile rinse liquid in the balloon and balloon lumen for a selected amount of time;

(i-1c) draining the sterile rinse liquid from the balloon and the balloon lumen;

(i-1d) repeating steps (i-1a)–(i-1c) until the amount of sterilant remaining in the balloon and the balloon lumen is below a selected threshold.

8. The method as recited in claim 7 wherein the balloon lumen is blocked to fluid flow prior to step (d), wherein the balloon lumen is unblocked to fluid flow prior to step (e), wherein the balloon lumen is blocked to fluid flow following step (i-1d), and wherein the balloon lumen is unblocked prior to step (i).

9. The method is set forth in claim 5 wherein the drying step includes;

simultaneously exposing the catheter to heat and a vacuum.

10. The method as set forth in claim 5 wherein the plasma or gaseous sterilant is selected from the class consisting of ethylene oxide, hydrogen peroxide, and peracetic acid.

11. A method of cleaning, decontaminating, and sterilizing a catheter having outer surfaces, a balloon, a dead-end balloon lumen open at a first end and closed by said balloon at a second end, and a guide wire lumen, said method comprising:

(a) cleaning and decontaminating the outer surfaces and the guide wire lumen of the catheter;

(b) cleaning, decontaminating, and sterilizing the interior of the balloon and the balloon lumen with a liquid sterilant;

(c) drying the catheter; and, (d) exposing the catheter to a gaseous or plasma sterilant.

12. The method as set forth in claim 11 wherein step (d) includes:

placing the catheter in a gas permeable bag; and contacting at least the outer surfaces and the guide wire lumen of the catheter with one of an ethylene oxide and a hydrogen peroxide vapor.

13. The method as set forth in claim 12 wherein at least one of steps (a) and (b) is implemented with a peracetic acid solution.

14. The method as set forth in claim 11 wherein step (a) includes:

blocking the balloon lumen; and contacting the outer surfaces and the guide wire lumen of the catheter with a liquid sterilant.

15. The method as set forth in claim 11 wherein step (b) includes:

(b1) rinsing the interior of the balloon and the balloon lumen with a sterile rinse liquid;

(b2) heating the liquid sterilant above room temperature;

(b3) communicating the heated liquid sterilant into the balloon lumen and the interior of the balloon;

(b4) retaining the liquid sterilant in the balloon and the balloon lumen for a selected duration;

(b5) draining the liquid sterilant from the balloon and the balloon lumen; and, (b6) repeating steps (b3)–(b5) until the interior of the balloon and the balloon lumen are sterilized.

* * * * *